US007468190B2

(12) United States Patent
Montaines et al.

(10) Patent No.: US 7,468,190 B2
(45) Date of Patent: Dec. 23, 2008

(54) **REDUCTION IN THE VIRULENCE OF *MYCOBACTERIUM TUBERCULOSIS* AND PROTECTION AGAINST TUBERCULOSIS BY MEANS OF *PHOP* GENE INACTIVATION**

(75) Inventors: Carlos Martin Montaines, Zaragoza (ES); Brigitte Giquel, Paris Cedex 15 (FR); Esther Perez Herran, Zaragoza (ES)

(73) Assignee: Universidad De Zaragoza, Zaragoza (ES)

( * ) Notice: Subject to any disclaimer, the term of this patent is extended or adjusted under 35 U.S.C. 154(b) by 0 days.

(21) Appl. No.: 10/485,372

(22) PCT Filed: Jul. 30, 2002

(86) PCT No.: PCT/ES02/00381

§ 371 (c)(1),
(2), (4) Date: Nov. 12, 2004

(87) PCT Pub. No.: WO03/012075

PCT Pub. Date: Feb. 13, 2003

(65) Prior Publication Data

US 2005/0106175 A1    May 19, 2005

(30) Foreign Application Priority Data

Jul. 31, 2001    (ES)    ................................ 200101824

(51) Int. Cl.
A61K 39/04    (2006.01)
A61K 49/00    (2006.01)
A61K 39/38    (2006.01)
C07H 21/02    (2006.01)
C07H 21/04    (2006.01)

(52) U.S. Cl. ...................... 424/248.1; 424/9.1; 424/9.2; 424/184.1; 424/234.1; 435/440; 435/471; 435/477; 536/23.1; 536/23.7

(58) Field of Classification Search .................. 424/9.1, 424/9.2, 184.1, 234.1, 248.1; 435/440, 471, 435/477; 536/23.1, 23.7
See application file for complete search history.

(56) References Cited

U.S. PATENT DOCUMENTS 5,424,065 A * 6/1995 Curtiss et al. .............. 424/93.2

FOREIGN PATENT DOCUMENTS

| WO | WO 9011687 A | 10/1990 |
| WO | WO 9502048 A | 1/1995 |
| WO | WO 9720033 A | 6/1997 |

OTHER PUBLICATIONS

Wren, B.W., et al. Degenerate PCR primers for the amplification of fragments from genes encoding response regulators from a range of pathogenic bacteria. FEMS Microbiology Letters, ((:287-292, 1992.*
Perez, E et al. "An essential role for *pho P* in *Mycobacterium tuberculosis* virulence" Molecular Microbiology 2001, vol. 41, No. 1, pàginas 179-187. Todo el documento.
Zahrt, T.C. et al. "An essential two component signal transduction system in *Mycobacterium tuberculosis*" Journal of Bacteriology, 2000, vol. 182, No. 13, pàginas 3832-3838. Todo el documento.
Zahrt, T.C. et al. "Elements of signal transduction in *Mycobacterium tuberculosis*: in vitro phosphrylation and in vivo expression of the response regulator MtrA" Journal of Bacteriology, 1996, vol. 178, No.11, pàginas 3314-3321. Todo el documento.
Zahrt, T.C. et al. "*Mycobacterium tuberculosis* signal transduction system required for persistent infectious". PNAS, 2001, vol. 98, No. 22 pàginas 12706-12711. Todo el documento.

* cited by examiner

*Primary Examiner*—Rodney P. Swartz
(74) *Attorney, Agent, or Firm*—Crowell & Moring LLP

(57) ABSTRACT

The construction of a mutant in the phoP gene by means of homologous recombination from a clinically isolated *Mycobacterium tuberculosis* reduces the virulence thereof in mouse bone marrow macrophage. Moreover, the phoP mutant reduces the virulence thereof in the experimental mouse model. Said phoP mutant can persist without being eliminated both in the macrophage and in the mouse. Mice inoculated with the phoP mutant are protected against *M. tuberculosis* infection. The use of mutants of mycobacteria in which the phoP gene or the genes regulated by phoP have been inactivated are candidates for vaccines against human and animal tuberculosis as well as possible recombinant vaccines against other pathogens.

1 Claim, 1 Drawing Sheet

REDUCTION IN THE VIRULENCE OF *MYCOBACTERIUM TUBERCULOSIS* AND PROTECTION AGAINST TUBERCULOSIS BY MEANS OF *PHOP* GENE INACTIVATION

CROSS-REFERENCE TO RELATED APPLICATIONS

This application is a 371(c) National Stage of PCT/ES02/00381 filed Jul. 20, 2002, which claims priority to Spanish patent application P 200101824 filed Jul. 31, 2001, the entire disclosures of which are incorporated herein incorporated by reference.

TECHNICAL FIELD

This invention pertains to the field of microbiology.

BACKGROUND OF THE INVENTION

Recent developments of genetic tools for manipulating the tuberculosis bacillus make possible the construction of mutants in specific genes.

In other intracellular pathogen microorganisms such as *Salmonella* it has been described that the phoP gene is involved in the virulence. Inactivation of this gene has permitted the construction of attenuated mutants, which have been studied as vaccines against Salmonellosis in humans.

Our preliminary results (University of Zaragoza) in strains of the *M. tuberculosis* complex isolated from humans have indicated that possibly the most virulent strains have an alteration of the gene annotated in the *M. tuberculosis* genome as phoP.

The gene was inactivated in clinical isolation for the purpose of studying the involvement of phoP in *M. tuberculosis* virulence and its multiplication ability and persistence in macrophage and mouse.

DESCRIPTION OF THE INVENTION

Vectors were constructed where the phoP gene of *M tuberculosis* was inactivated by the introduction of a gene resistant to kanamicin. The vectors were transformed into a clinical isolate of *M tuberculosis* and a strain with the inactivated phoP gene was obtained.

Work relating to these constructions was recorded in the 1998-1999 workbooks of the Genetics Mico-bacteria Group laboratories of the University of Zaragoza and the Unité de Génétique Mycoctérienne of the Pasteur Institute of Paris.

The phoP mutant of *M. tuberculosis* has been deposited in the culture collection of the Pasteur Institute of Paris (I-2622), 28, rue du Dr. Roux, 75724 Paris Cedex 15, France, on Nov. 27, 2000.

When *M. tuberculosis* was studied and compared with the mutant *M. tuberculosis* phoP strain for 7 days in mouse bone marrow macrophages, it was observed that the mutant was not able to replicate in mammal macrophage. By continuing with the culture of the mutant for 14 days, it was observed that it was able to persist.

After infecting a mouse with the mutant strain, it was observed that there is no multiplication of the bacillus at 3 weeks or at 6 weeks, but the number of bacteria in the spleen, the liver, and the lungs is not reduced as compared with the initial inoculation.

The results of experiments with the *M. tuberculosis* phoP in macrophage and mouse are contained in the workbooks of the Genetics Mico-bacteria Group laboratories of the University of Zaragoza and the Unité de Génétique Mycoctérienne of the Pasteur Institute of Paris for the year 2000.

The mouse protection studies discussed below under the Description of Figures should be considered with these results. The *M. tuberculosis* phoP mutant was inoculated subcutaneously. Eight weeks later, the mice were intravenously infected with *M. tuberculosis* H37Rv. Bacterial count 4 weeks after infection clearly shows that the phoP mutant protects against the multiplication of *M. tuberculosis* with an effectiveness comparable to the BCG vaccine control. The results of the experiments are contained in the workbooks of the Unité de Génétique Mycoctérienne of the Pasteur Institute of Paris for the years 2001-2002.

Balb/c mice were inoculated subcutaneously with $10^7$ colony forming units (CFUs) either of BCG control vaccine against tuberculosis or of candidate for vaccine of the *M. tuberculosis* phoP mutant.

Figure 1:
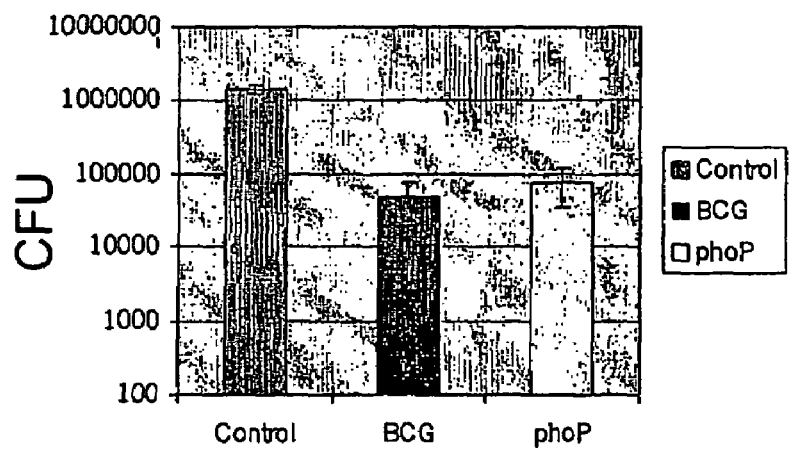
FIG. 1 shows the protection of the *M. tuberculosis* phoP mutant against infection with *M. tuberculosis* H37Rv.
Figure 1:
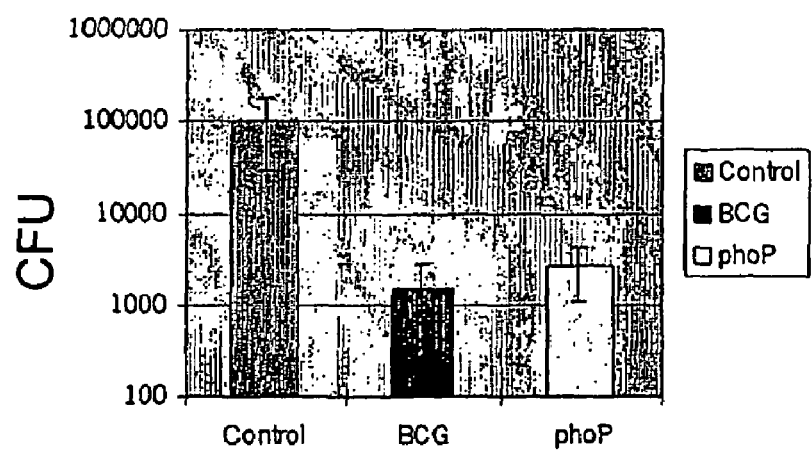

Eight weeks later, the mice were infected intravenously with *M. tuberculosis* H37Rv ($10^5$ CFUs). Four weeks after infection, the animals were sacrificed and CFUs were counted in the spleen (FIG. 1A) and the lungs (FIG. 1B). Each value represents the geometric average±SEM.

The invention claimed is:

1. A *Mycobacterium tuberculosis* strain with an inactivated phoP gene which causes the strain to have attenuated virulence.

* * * * *